United States Patent [19]

Speights et al.

[11] Patent Number: 5,032,579

[45] Date of Patent: Jul. 16, 1991

[54] METHOD FOR INHIBITING THE GROWTH OF SALMONELLA

[75] Inventors: Robert M. Speights, Arvada; Peter J. Perna, Boulder; Steven L. Downing, Louisville, all of Colo.

[73] Assignee: Coors Biotech, Inc., Westminster, Colo.

[21] Appl. No.: 558,106

[22] Filed: Jul. 25, 1990

Related U.S. Application Data

[63] Continuation of Ser. No. 433,506, Nov. 9, 1989, which is a continuation of Ser. No. 107,115, Oct. 13, 1987, Pat. No. 4,902,674.

[51] Int. Cl.$^5$ .................. A61K 31/70; A61K 33/00
[52] U.S. Cl. .................................. 514/23; 514/867; 424/92; 424/442; 426/2; 426/658
[58] Field of Search .............. 514/23, 867; 426/2, 426/658; 424/92, 442

[56] References Cited

U.S. PATENT DOCUMENTS

| | | | |
|---|---|---|---|
| 3,701,714 | 10/1972 | Okada et al. | 435/97 |
| 3,703,440 | 11/1972 | Okada et al. | 435/97 |
| 3,728,132 | 4/1973 | Tsuyama et al. | 426/48 |
| 3,819,484 | 6/1974 | Okada et al. | 435/97 |
| 3,894,146 | 7/1975 | Tsuyama et al. | 426/658 |
| 3,931,398 | 1/1976 | Gaffar et al. | 424/92 |
| 4,024,251 | 5/1977 | Maiese et al. | 435/886 |
| 4,133,875 | 1/1979 | Hillman | 424/93 |
| 4,160,026 | 7/1979 | Iwamatsu et al. | 435/84 |
| 4,276,379 | 6/1981 | Heady | 435/94 |
| 4,312,856 | 1/1982 | Korduner et al. | 424/145 |
| 4,316,894 | 2/1982 | Omoto et al. | 514/23 |
| 4,335,107 | 6/1982 | Snoeyenbos et al. | 426/61 |
| 4,374,154 | 2/1983 | Cole et al. | 426/565 |
| 4,401,662 | 8/1983 | Lormeau et al. | 514/56 |
| 4,435,389 | 3/1984 | Mutai et al. | 514/54 |
| 4,496,550 | 1/1985 | Lindahl et al. | 514/54 |
| 4,581,227 | 4/1986 | Kjelleberg et al. | 514/474 |
| 4,681,771 | 7/1987 | Adachi et al. | 426/658 |
| 4,689,226 | 8/1987 | Nurmi et al. | 426/2 |
| 4,693,898 | 9/1987 | Nakatomi et al. | 426/19 |
| 4,726,948 | 2/1988 | Prieels et al. | 514/867 |
| 4,734,402 | 3/1988 | Hashimoto et al. | 514/54 |
| 4,762,822 | 8/1988 | Ettinger | 514/25 |

FOREIGN PATENT DOCUMENTS

| | | |
|---|---|---|
| 06695 | 1/1980 | European Pat. Off. |
| 133547 | 2/1985 | European Pat. Off. |
| 171026 | 2/1986 | European Pat. Off. |
| 188047 | 7/1986 | European Pat. Off. |
| 1336002 | 11/1973 | United Kingdom |
| 1352633 | 5/1974 | United Kingdom |
| 1390065 | 4/1975 | United Kingdom |
| 2072679 | 10/1981 | United Kingdom |
| 2105338 | 3/1983 | United Kingdom |
| 2179946 | 3/1987 | United Kingdom |

OTHER PUBLICATIONS

"Nondigestibility of a New Sweetner, 'Neosugar,' in the Rat," Oku et al., Journal of Nutrition, vol. 114, No. 9, pp. 1574–1581 (1984).

"Microbial Colonization Control of Chicken Intestine Using Defined Cultures", S. Stavric, Food Technology 41(7), Jul. 1987, pp. 93–98.

"Substrate Specificity of Fructosyl Transferase from Chicory Roots", Singh, et al., Phytochemistry, 1971, vol. 10, pp. 2037–2039.

"Sucrose: Sucrose Fructosyltransferase and Fructan: Fructan Fructosyltransferase from Allium Sepa", Phytochemistry, 1980, vol. 19, pp. 1017–1020.

"Production of Several Oligosaccharides from Sucrose by the Action of an Aspergillus Enzyme Preparation and Structural Studies of the Products", Kyoritsu Yacka Daigaku Kenkyu Nempe, vol. 20, 1975.

The Greeley (Colo.) Daily Tribune, "Sugar Stops Bacteria in Poultry", Apr. 12, 1989, p. C6.

The Difco Manual of Dehydrated Culture Media and Reagents, Ninth Edition, 1953, pp. 134–138.

The Merck Index, An Encyclopedia of Chemicals and Drugs, Ninth Edition, 1976, p. 842.

Breed et al., Bergey's Manual of Determinative Bacteriology (6th ed), vol. 1, p. 503 (1948).

Bergey's Manual of Systematic Bacteriology, vol. 1, p. 415 (1984).

Gutnick et al., "Compounds Which Serve as the Sole Source of Carbon or Nitrogen for *Salmonella* Typhimurium LT-2", J. Bacteriol., vol. 100, p. 215 (1969).

Hidaka et al., "Effect of Fructo-Oligosaccharides on Human Intestinal Flora" (1984) (Japanese Reference).

"USDA Promotes Lactose, D-Mannose to Prevent Salmonella in Chickens", Food *Chemical News*, p. 27 (Apr. 3, 1989).

(List continued on next page.)

Primary Examiner—Ronald W. Griffin
Attorney, Agent, or Firm—Sheridan, Ross & McIntosh

[57] ABSTRACT

A method and composition for the inhibition of growth of Salmonella is provided. The effective composition of the invention is a composition which is fermented by microflora other than Salmonella at a rate competitively greater Salmonella or which is fermented by microflora other than Salmonella to produce metabolites which inhibit the growth of Salmonella. In one embodiment of the present invention, the effective composition is a class of fructo-oligosaccharides which inhibit the growth of Salmonella. More particularly, the fructo-oligosaccharidesa are sucrose molecules having from 1 to 8 fructose residues. This class of sugars is exemplified by "Neosugar" which includes 1-kestose, nystose, and 1-fructofuranosyl-nystose. The present method includes contacting Salmonella with the effective composition and can include feeding it to a domestic food anomal. The present composition includes the effective component and nutritive feed material.

34 Claims, No Drawings

OTHER PUBLICATIONS

"Milk Products Could Get Salmonella Boost", *Feed Business Report*, vol. 2, No. 4, (Apr. 1989).

Bailey et al., Effect of Anticoccidial and Antimicrobial Feed Additives on Prevention of Salmonella Colonization of Chicks Treated With Anaerobic Cultures of Chicken Feces, Avian Disease, vol. 32, pp. 324–329 (1988).

"Sugar can cut Chicken Bacteria", The Pentagraph (of Bloomington, Ill.), Highlights sec. (Mar. 28, 1989).

"Sugar May Be Key to Reducing Salmonella Bacteria In Chickens", State Journal–Register (of Springfield, Ill.) (Mar. 30, 1989).

Assoc'd. Press, "A Spoonful of Sugar For Hens?", (Mar. 28, 1989) and USDA: Sugar Can Cut Salmonella (Mar. 27, 1989) (copyrighted news stories).

"A Sweet Salmonella Fighter", Kiplinger Agriculture Letter (May 5, 1989).

Corn Refiners Ass'n., "Research Hints at Further Corn Uses", Corn Capsules (May 2, 1989).

"Sweet Solution to Tainted Poultry", Science News (Jun. 3, 1989).

"Sweet Treatment for Poultry Salmonella", Insight (May 8, 1989) and Wash. Times (May 31, 1989).

"A Spponful of Sugar Keeps the Salmonella at Bay", New Scientist, Technology sec. (Jun. 17, 1989).

"Milk Might Put an End to the Great Salmonella Scare", Business Week, Developments to Watch sec. (Aug. 21, 1989).

"Lactose in Chicken Feed May Prevent Salmonella Colonization, ARS Reports", Food Chemical News, p. 12 (Dec. 19, 1988).

"Salmonella Prevention with Carbohydrates", Broiler Indus. pp. 8–10 (Sep. 1989).

"Sugars Slash Chances of Poultry Contamination", USDA News (Mar. 27, 1989).

METHOD FOR INHIBITING THE GROWTH OF SALMONELLA

This is a continuation of application Ser. No. 07/433,506, filed Nov. 8, 1989, which is a continuation-in-part of Ser. No. 07/107,115 filed Oct. 13, 1987 which issued as U.S. Pat. No. 4,902,674 on Feb. 20, 1990.

FIELD OF THE INVENTION

The present invention relates generally to the inhibition of growth of Salmonella. More specifically, the invention relates to a method for inhibiting the growth of Salmonella in the intestines of food animals to prevent Salmonella infections in humans. As used herein, reference to the term "prevent Salmonella infections" and similar terms means the reduction of the overall risk of infection throughout a given population.

BACKGROUND OF THE INVENTION

Certain species of Salmonella bacteria are well known human pathogens. The most common means of human infection is by ingestion of contaminated foods. Many species of Salmonella are recognized as common microflora in the intestines of food animals, such as poultry and beef.

Various compositions are known for treatment of Salmonella poisoning in humans. For example, chloramphenicol, ampicillin, and trimethoprim-sulfa, are known to be effective against Salmonella organisms. While such compositions are generally useful against Samonella, the ideal method for controlling Salmonella poisoning is prevention of infection. Proper cleaning of meat and dairy products and thorough cooking can prevent human infection by Salmonella.

One embodiment of the present invention is a method for controlling Salmonella poisoning in humans by inhibiting the growth of Salmonella populations in food animals. In this manner, fewer organisms are present in the food animals, and therefore, the chance of transmission to humans is smaller. This method involves introducing an effective compound for the inhibition of growth of Salmonella to the intestinal tract of food animals.

Specific embodiments of the effective compound of the present method are produced by Meiji Seika Kaisha, Ltd. under the trade name "Neosugar". For example, in Oku et al., *Nondigestibility of a New Sweetener, "Neosugar,"* in the Rat, J. of Nutrition, v. 114, No. 9, pp. 1575-81 (1984), Neosugar is described as a mixture of 1-kestose, nystose, and 1-fructofuranosyl nystose which was studied for digestibility in rats. See also U.S. Patent No. 4,681,771 to Adachi, et al. (July 21, 1987), U.K. Patent No. GB 2,072,679 and U.K. Patent No. GB 2,150,338, owned by Meiji Seika, which discuss the use of Neosugar compositions as low-cariogenic and low-calorie sweeteners.

Similar compounds are known for a variety of other uses. In European Patent Application No. 85300340.8, filed on Jan. 18, 1985, a process for preparing a compound termed "fructo-oligosaccharose" was disclosed. The process involves culturing an *Aureo-bacidium* species to produce the enzyme fructosyl-transferase. The culture medium is then contacted with sucrose to provide a substrate for the production of this fructo-oligosaccharose by the enzyme.

European Patent Application No. 84109126.7, Publication No. 0133547, describes an animal feed for preventing scours (diarrhea) which includes fructo-oligosaccharides produced by the action of fructosyl transferase on sucrose.

U.S. Pat. No. 4,496,550 to Lindahl, et al. (Jan. 29, 1985) and U.S. Pat. No. 4,401,662 to Lormeau, et al. (Aug. 30, 1983) discuss the use of mixtures of oligosaccharides to counteract or prevent coagulation of blood to prevent arterial thrombosis.

U.S. Pat. No. 3,701,714 to Shigetaka (Oct. 31, 1972) and U.S. Pat. No. 3,703,440 to Shigetaka (Nov. 21, 1972) discuss the use of oligosaccharides as the main constituent for use as a starch syrup. U.S. Pat. No. 3,728,132 to Tsuyama, et al. (Apr. 17, 1973) and U.S. Pat. No. 3,894,146 to Tsuyama (July 8, 1975), discuss the use of oligosaccharides as a low cariogenic sweetener.

U.S. Pat. No. 4,435,389 to Mutai, et al. (Mar. 6, 1984) discusses an oligosaccharide composition for promoting the growth of Bifidobacteria in human intestines. The oligosaccharide composition has a general formula of Gal-(gal)n-Glc, wherein "Gal" denotes a galactose residue, "Glc" a glucose residue, and "n" an integer of one to four. Bifidobacteria is a bacteria living in the human intestines with known beneficial physiologial affects.

U.S. Pat. No. 4,160,026 to Iwamatsu (July 3, 1979) describes antibiotic oligosaccharides termed SF-1130-$x_1$ and SF-1130-$x_2$ which are produced by the fermentation of *Streptomyces myxogenes* SF-1130. Toxicity against a number of microorganisms, including Salmonella, as tested by formation of inhibition zones from paper discs impregnated with the compounds was disclosed. These substances are described as active antibiotic substances against gram-negative bacteria.

U.S. Pat. No. 4,316,894 to Omoto, et al. (Feb. 23, 1982) discloses a compound designated as SF-1130-$x_3$ having a disclosed utility as a drug for suppressing blood sugar elevations after ingesting starch and/or sugars and as a weak antibacterial compound. Although a chemical structure is not provided, antibacterial activity was demonstrated in *E. coli*. SF-1130-$x_3$ is described as an oligosaccharide and detailed chemical characterizations of the substance are provided. SF-1130-$x_3$ is produced by fermentation of Streptomyces bacterial.

In view of the above, a new method for inhibiting the growth of Salmonella is highly desirable. Such a method is useful for controlling or limiting the population of Salmonella in the intestines of food animals as a means for preventing human Salmonella infections.

SUMMARY OF THE INVENTION

The present invention includes a method and composition for inhibiting the growth of Salmonella. In the method, a composition including an effective composition is contacted with the Salmonella to inhibit growth.

The effective composition is a composition which is fermented by microflora other than Salmonella at a rate competitively greater than Salmonella or which is fermented by a microflora other than Salmonella to produce metabolites which inhibit the growth of Salmonella. In one embodiment of the present invention, the effective composition includes fructo-oligosaccharides.

The fructo-oligosaccharides are more specifically characterized as sucrose molecules having from 1 to 8 fructose residues. This class of compounds is exemplified by a product, Neosugar, which includes as components 1-kestose, nystose, and 1-fructofuranosylnystose.

A particular embodiment of the invention includes feeding the composition to a food animal to inhibit the growth of Salmonella in the intestines of the animal. A further embodiment includes feeding the composition to an animal having intestinal Salmonella which cannot ferment and intestinal microflora, such as Lactobacillus or Streptococcus, which can ferment the effective composition. In this method, Salmonella are competitively inhibited by the enhanced growth of other bacteria.

Another aspect of the present invention is a feed composition for the inhibition of intestinal Salmonella in food animals. The composition has a nutritive component and a component which includes the effective composition in an amount effective to inhibit the growth of Salmonella.

DETAILED DESCRIPTION

One aspect of the present invention involves a method for inhibiting the growth of Salmonella. A particular application of the invention is the inhibition of Salmonella in the intestines of animals for the prevention of infection of humans who later ingest food products from the animals. Another aspect of the invention is a feed composition for the inhibition of intestinal Salmonella in food animals. Generally, the effective composition in the method and feed composition is a composition which is fermented by micriflora other than Salmonella at a rate competitively greater than Salmonella or which is fermented by microflora other than Salmonella to produce metabolites which inhibit the growth of Salmonella. In one embodiment of the present invention, the effective composition is a mixture of fructo-oligosaccharides which inhibits growth of species of Salmonella. It is believed that inhibition occurs due to the inability of Salmonella to ferment the effective composition. The effective composition and specific embodiments of the effective composition will be discussed in more detail below. However, for the present, all embodiments will be generally referred to as the "effective composition."

The method for inhibiting the growth of Salmonella includes contacting a population of Salmonella with the effective composition. It has been found that in the presence of the effective composition, with only minimal amounts of carbohydrate sources other than the effective composition available, Salmonella fermentation activity is limited. The fermentation which does occur is thought to be fermentation of small quantities of glucose present in the medium. While not wishing to be bound by theory, it is believed that the lack of fermentation activity is due to the inability of Salmonella to break down components of the effective composition into smaller sugar units or to otherwise effectively metabolize the effective composition. Therefore, according to this theory, in an environment where the effective composition is present, growth of Salmonella is inhibited by reduced carbohydrate availability. If the carbohydrate source of the environment consists primarily of the effective composition, inhibition is very strong. If the environment has other carbohydrate sources which can be used by Salmonella, inhibition occurs, but at a lower level.

The embodiment of the effective composition discussed above appears to inhibit growth of Salmonella due to the inability of the organism to ferment the effective composition or to otherwise effectively metabolize the effective composition. It should be noted, however, that other effective compositions may inhibit Salmonella growth by other mechanisms, e.g. toxicity or as discussed below, by the production of metabolites upon fermentation of the composition by microflora other than Salmonella which inhibit the growth of Salmonella. Such other compositions are specifically contemplated and are considered to the within the scope of the present invention.

A particular embodiment of the present method involves introducing the effective composition to the intestinal tract of a food animal. A wide variety of microflora are present in the intestines of all animals. In the intestines of many animals from which humans derive food, populations of pathogenic Salmonella are present without any deleterious effects to the animals. However, transmission of a sufficient number of Salmonella organisms to a human can cause serious illness. By introducing the effective composition to the intestines of a food animal, the balance of intestinal microflora is shifted away from Salmonella in favor of other species of microflora. In this manner, the likelihood of transmission of Salmonella organisms to humans from food animals is reduced because the initial Salmonella population is smaller.

The present method is particularly effective, in one embodiment, when microflora which are not pathogenic to humans and which can ferment the effective composition are present in the intestines of the food animal. In such animals, growth of Salmonella is competitively inhibited by the enhanced growth of other microflora. For example, it has been found that the effective composition can be fermented by Lactobacillus and Streptococcus. These microorganisms are commonly found in many food animals and will not cause human illness. Poultry are known to have Salmonella, Lactobacillus and Streptococcus populations in their intestines. By introducing the effective composition to poultry, the growth of non-pathogenic microflora is enhanced and the population of Salmonella decreases. The overall balance of microflora in the intestines of the poultry will be shifted in favor of bacteria not harmful to humans, Lactobacillus and Streptococcus. The likelihood of human infection by Salmonella is thereby decreased because the source population of Salmonella is reduced.

In another embodiment of the present method, the effective composition is fed to a food animal and fermented by intestinal microflora other than Salmonella to produce metabolites that are secreted into the intestinal environment to inhibit the growth of intestinal Salmonella. In this manner, growth of Salmonella is competitively inhibited by the metabolic production of other microflora to shift the overall balance of intestinal microflora away from Salmonella.

Without wishing to be bound by theory, it is believed that metabolites secreted by microflora other than Salmonella can inhibit the growth of Salmonella by various mechanisms. For example, metabolites produced by such other microflora can change the pH of the intestinal environment which can result in a reduced ability of Salmonella to grow or survive in the intestines. Alternatively, such other microflora can produce metabolites which are antibiotics that inhibit the growth of or kill Salmonella. The term "antibiotic" refers to a chemical substance produced by a microorganism that inhibits the growth of or destroys other microorganisms.

The effective composition of the present invention includes compositions which are fermented by microflora other than Salmonella at a rate competitively greater than Salmonella or which are fermented by microflora other than Salmonella to produce metabolites which inhibit the growth of Salmonella. In one embodiment of the present invention, the effective composition includes fructo-oligosaccharides which cannot be fermented by Salmonella. "Fructo-oligosaccharide", as used herein, refers to a trisaccharide having one or more additional fructose residues. This class includes mixtures of oligosaccharide molecules comprised of sucrose having from 1 to 8 fructose residues. The fructose residues are preferably attached by a beta 2-1 bond. The class is exemplified by the fructo-oligosaccharides in the Neosugar produced by Meiji Seika and as described in U.S. Pat. No. 4,681,771, which is incorporated by reference herein.

Neosugar is a mixture including 1-kestose, nystose, and 1-fructofuranosyl-nystose. Neosugar, as used herein, is more particularly defined as having between about 20% by weight and about 40% by weight 1-kestose, between about 20% by weight and about 55% by weight nystose, and between about 5% by weight and about 15% by weight 1-fructofuranosyl-nystose. The remaining portion of a Neosugar mixture can include between about 4% by weight and about 45% by weight of a mixture of glucose and sucrose. In one form, Neosugar G, the composition is a 75% syrup having between about 40% by weight and about 50% by weight of a mixture of glucose and sucrose, between about 20% by weight and about 30% by weight 1-kestose, between about 20% by weight and about 30% by weight nystose, and between about 2% by weight and about 8% by weight 1-fructofuranosyl-nystose. In another form, Neosugar P, the composition is either a 75% syrup or a powder having between about 2% by weight and about 6% by weight of a mixture of glucose and sucrose, between about 30% by weight and about 40% by weight 1-kestose, between about 45% by weight and about 55% by weight nystose, and between about 5% by weight and about 15% by weight 1-fructofuranosyl-nystose. The structures of 1-kestose, nystose, and 1-fructofuranosyl-nystose are provided below.

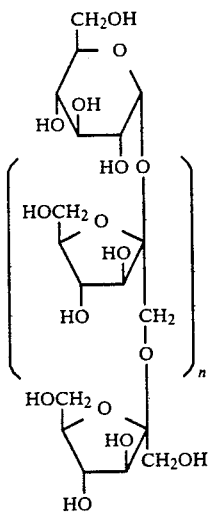

where:
n=1 for 1-kestose
n=2 for nystose
n=3 for 1-fructofuranosylnystose

Neosugar can be produced by the action of fructosyl-transferase on sucrose to produce a mixture of 1-kestose, nystose, and 1-fructofuranosyl nystose. Neosugar G, for example, can be produced by subjecting the product of fructosyl-transferase activity to decoloration, filtration, desalting, and concentration. Neosugar G can be further purified with an ion exchange resin to produce Neosugar P. Although these methods produce mixtures of fructo-oligosaccharides, it is contemplated that the use of the pure compounds which are in Neosugar are within the scope of the invention.

Certain fungi, such as, Aspergillus and Aureobasidium are known to produce the enzyme fructosyltransferase. Fructosyl transferases which produce oligosaccharides are known to be produced by chicory plant and by onion plant. See Singh et al., *Substrate Specificity of Fructosyl Transferase From Chicory Roots*, Phytochemistry vol. 10, pp. 2037-39 (1971) and Henry et al., *Sucrose:Sucrose Fructosyltransferase and Fructan:-Fructan Fructosyltransferase From Allium Cepa*, Phytochemistry vol. 19, pp. 1017-20 (1980).

In addition to fructooligosaccharides such as Neosugar, the effective composition of the present method can also include any composition having similar functional properties of fructooligosaccharides, i.e., being fermented by microflora other than Salmonella at a rate competitively greater than Salmonella. The determination of whether a composition is an effective composition that functions in this manner is a matter of routine testing. For example, one can design and conduct routine tests to determine whether a particular composition is fermented by Salmonella and microflora other than Salmonella at rates for which the microflora other than Salmonella have a competitive advantage. Tests such as the acid production and growth tests illustrated in Examples 1-13 below will identify effective compositions. Further, to reduce the amount of testing to identify effective compositions, one can consult the relevant literature to identify compositions that are non-fermentable by Salmonella or are fermentable by other intestinal microflora. Such references provide a starting point for further testing to identify whether the composition is otherwise suitable for use in the present invention.

Literature references which identify compositions that are either not readily fermented by Salmonella or are fermented by other intestinal microflora include Breed et al., Bergey's Manual of Determinative Bacteriology (6th ed.), Vol. 1, p. 503 (1948); Bergey's Manual of Systematic Bacteriology, Vol. 1, p. 415 (1984); Gutnick et al., "Compounds Which Serve as the Sole Source of Carbon or Nitrogen for *Salmonella typhimurium LT-2*", J. Bacteriol., Vol. 100, p. 215 (1969); and Hidaka et al., "Effect of Fructooligosaccharides on Human Intestinal Flora" (1984).

For example, Breed et al., discloses that *Salmonella typhimurium* does not produce acid or gas from, i.e., does not ferment, the following compositions: lactose, sucrose, raffinose, inulin, salicin or adonitol. One can test any of these compositions to determine if they are fermentable by other intestinal microflora such as, e.g., Lactobacillus or Streptococcus, in the manner described in Examples 1-13 below. Similarly, Bergey's Manual of Systematic Bacteriology (1984) discloses that Salmonella I does not ferment, among other compositions, lactose, sucrose, salicin, D-adonitol, and raffinose; Salmonella II does not ferment, among other compositions, lactose, sucrose, raffinose and cellobiose; and Salmonella III does not ferment, among other compositions, sucrose, dulcitol, salicin and myoinositol. Any of the compositions identified as non-fermentable by the three Salmonella strains can be tested to determine whether they are fermentable by other intestinal microflora.

The compounds of Table 3 of Gutnick et al. are identified as not serving as a sole carbon or a sole nitrogen source for *Salmonella typhimurium*. These compounds can be tested to determine if they are fermentable by other intestinal microflora. Those found to be non-fermentable by *Salmonella typhimurium* and fermentable by other intestinal microflora can be used in the present method for the inhibition of Salmonella.

The compounds of Table 5 of Hidaka et al., are indicated as being fermentable by a number of intestinal microflora including Bifidobacterium, Lactobacillus, Eubacterium, Propionibacterium, Bacterioides, Megamonaas, Mitsuokella, Clostridium, Fusobacterium, Sphaerophorus, Escherichia, Klebsiella, Streptococcus and Peptococcus. These compounds can be tested to determine if any inhibit Salmonella growth.

The effective composition further includes compositions which are fermented by intestinal microflora other than Salmonella to produce metabolites which inhibit the growth of Salmonella. The determination of whether a composition is an effective composition that functions in this manner is a matter of routine testing. For example, one can conduct plating experiments in which the control plate includes the proposed effective composition and Salmonella and the test plate includes the proposed effective composition, Salmonella and some non-pathogenic intestinal microflora. If the results indicate that Salmonella growth occurs in the control plate but not in the test plate, then one can conclude that the combination of the other microflora and the proposed effective composition inhibits the growth of or kills the Salmonella by the mechanism of the effective composition being fermented by the microflora in the test plate and the microflora producing a metabolite that inhibits the growth of or kills the Salmonella.

If, in the above experiment, no growth occurs in the control plate, then one can conclude that Salmonella is unable to use the proposed effective composition as a carbon or energy source. In this event, a second experiment can be conducted using some carbon and energy source which Salmonella can use. The test plate in such an experiment would include the following: (i) Salmonella; (ii) some non-pathogenic intestinal microflora; (iii) carbon/energy source; and (iv) proposed effective composition. If Salmonella does not grow in such a plate and the following four controls all have the indicated results, one can conclude that growth of the other microflora using the proposed effective composition produces metabolites to inhibit the growth of or kill the Salmonella. The four control plates are as follows:

| Plate No. | Components | Result | Interpretation |
|---|---|---|---|
| 1 | Salmonella carbon/energy source | Salmonella growth | Sal. utilizes the carbon/energy source |
| 2 | Salmonella carbon/energy source effective composition | Salmonella growth | Proposed effective composition does not independently inhibit Sal. growth |
| 3 | other microflora proposed effective composition | other microflora growth | Other microflora can metabolize proposed effective composition |
| 4 | Salmonella other microflora | Salmonella growth | Metabolism of carbon/energy source by other microflora does not |

-continued

| Plate No. | Components | Result | Interpretation |
|---|---|---|---|
| | | | produce metabolites that inhibit growth of Salmonella |

It should be appreciated that other similar experiments can be conducted to ascertain whether a proposed effective composition functions by being fermented by microflora other than Salmonella to produce metabolites which inhibit the growth of or kill Salmonella.

Once compositions are identified as being fermented by microflora other than Salmonella at a rate competitively greater than Salmonella or as being fermented by microflora other than Salmonella to produce metabolites which inhibit the growth of or kill Salmonella, the composition can readily be used in the present method for selectively inhibiting the growth of intestinal Salmonella in the presence of intestinal microflora other than Salmonella in a food animal in the same manner as fructooligosaccharides.

In a preferred embodiment of the present method, the effective composition is fed to a food animal where the inhibition of the growth of intestinal Salmonella will occur. The preferred method of introduction is to mix the effective composition with nutritive feed material or water supplies for the animal. It is contemplated, however, that the effective composition can either be mixed with the nutritive feed material or water or fed to the animal separately. In either embodiment, the effective composition must be provided in an amount effective to inhibit the growth of Salmonella. This amount will vary depending upon the size of the food animal. Poultry will require smaller quantities of the effective composition than, for example, beef to inhibit intestinal Salmonella. Effective amounts can readily be determined by experimentation.

In practice of the present method by feeding the effective composition to food animals to inhibit intestinal Salmonella populations, it is not necessary to practice the method for the entire life of the animal. The primary concern of the food industry is to prevent transmission of Salmonella to humans. Therefore, limiting the Salmonella population to a minimum by the present method just prior to slaughter of the food animal is sufficient to reduce the likelihood of transmission to the human population. In this manner, costs attendant to the present process can be minimized.

The feed composition of the present invention includes, as one component, the effective composition. The feed composition also includes some material which is nutritive for the animal to which the feed composition is fed. Typically, for most food animals, such as poultry or beef, the nutritive material is some type of grain product. It is contemplated that the majority of the feed composition can be nutritive material with the effective composition present in an amount sufficient to inhibit growth of intestinal Salmonella. Typically, the effective composition is present in an amount between about 0.05% by weight and about 5% by weight and more preferably between about 0.25% by weight and about 3% by weight and most preferably between about 0.25% by weight and about 1% by weight. When the effective composition is administered to a food animal in the water supply, it should be included in the same weight percentages as indicated for inclusion with the feed composition.

The method and composition of the present invention can be used for inhibiting the growth of Salmonella in a wide variety of animals from which humans obtain food. Many such animals are known to have intestinal Salmonella populations, and therefore, can potentially contaminate any meat or dairy products consumed by humans. Accordingly, the present method and composition are contemplated for use with any type of food animal, including but not limited to, poultry, beef, pork, and lamb. The term "poultry" is meant to include, but not be limited to, chickens, ducks, turkeys, geese, quail, and cornish game hens.

Another aspect of the present invention is a method for reducing or preventing the intestinal colonization of food animals by Salmonella which includes introducing the effective composition to the intestinal tract of a food animal and also introducing a competitive exclusion culture to the intestinal tract of the food animal. As used herein with reference to the use the competitive exclusion cultures, the term "reducing" shall refer to the concept of preventing as well. The term "competitive exclusion" refers to a recognized method of preventing the intestinal colonization of young food animals by pathogenic bacteria, such as Salmonella. This method is discussed, for example, in Stavric, *Microbial Colonization Control of Chicken Intestine Using Defined Cultures*, Food Technology 41(7), pp. 93–98, Jul. 1987, which is incorporated herein in its entirety by reference.

Competitive exclusion involves the introduction of a culture of normal adult intestinal microflora into the intestines of a young animal to protect against the colonization of the intestines of the young animal by undesirable microorganisms, such as Salmonella. Typically, when animals are born, few genera of microorganisms are present in the gut. Native adult microflora, however, become established in poultry, for example, in the small intestine within about two weeks and in the ceca within about four weeks. In modern breeding methods food animals are often reared in the absence of adult animals and the normal, healthy gut microflora which would naturally be transferred from adults to the young are absent in the environment of the young animals. Animals raised under such conditions are particularly susceptible to gut colonization by pathogenic bacteria, such as Salmonella. By providing competitive exclusion cultures to newborn animals, the establishment of normal adult microflora to the exclusion of Salmonella or other harmful bacteria is facilitated.

Introduction of the competitive exclusion culture into the young animals should occur early in the lift of the animal so that the introduced culture has time to become established prior to challenge by an unwanted culture of pathogenic bacteria. For example, as discussed in Stavric, it has been found that chicks can be successfully made resistant to Salmonella infection by innoculating one to two day old chicks with an undefined culture from healthy adult Salmonella-free chickens.

Competitive exclusion cultures are either "defined" or "undefined". Undefined cultures refer to microflora cultures which are taken from the intestines of healthy adult animals having established intestinal microflora and which are not infected by Salmonella. For example, it has been found that chickens reared under normal conditions develop fully protective intestinal microflora cultures within about three to five weeks. Defined competitive exclusion cultures refer to bacterial cultures in which the genera of bacteria in the culture are known. Defined cultures of a single species of bacteria have been experimented with, as well as defined cultures including numerous species of bacteria. Competitive exclusion cultures whether defined or undefined are introduced orally to the treated animal.

By using competitive exclusion techniques in conjunction with the introduction of the effective composition to young food animals, intestinal colonization of Salmonella is reduced. As discussed above, competitive exclusion cultures are preferably provided early in the life of an animal, and in the instance of chickens, are preferably provided within the first two days of life. As discussed above, the present method of feeding the effective composition to food animals to inhibit intestinal Salmonella populations, can be conducted either throughout the entire life of the food animal or only during a portion thereof. For example, if administration of a competitive exclusion culture is used, feeding of the effective composition can be conducted during the first several days or several weeks of life around the time the competitive exclusion culture is being adminstered. Alternatively, the effective composition can be fed to the food animal throughout its entire life while the competitive exclusion culture is administered as discussed above, i.e., within the early part of the life of the animal. Another alternative is to feed the effective composition to the food animal either just prior to slaughter of the food animal or, for example, during the initial several days or several weeks of life while the competitive exclusion culture is being administered and during the time period just prior to slaughter of the food animal.

Another aspect of the present invention includes the use of feeding the effective composition to food animals in a "shuttle program" with antibiotics to reduce the colonization or growth of Salmonella populations in the food animals' intestinal tract. Such a shuttle program involves the alternating use of the effective composition and one or more orally administered antibiotics. The antibiotics used in a shuttle program can include any antibiotic which is recognized as being effective against Salmonella or which hereafter becomes recognized as being effective against Salmonella. Such antibiotics include, without limitation, chloramphenicol, ampicillin, trimethoprim-sulfa, and mixtures thereof.

The effective composition and any antibiotics used can be administered according to various time schedules. For example, the effective composition and the antibiotic[s] can be administered simultaneously or serially. The required frequency of administrations depends upon the conditions to which the food animals are exposed. Under conditions in which the food animals are often exposed to strong Salmonella challenges and other environmental stress, such as extreme heat or cold or overcrowded conditions, the frequency of administrations should be greater. The frequency of administration of a shuttle program using the effective composition and antibiotics can be the same as that for typical antibiotic administration programs. The administration of the effective composition and antibiotics can be provided serially with time periods between administrations varying from several minutes to several hours to several days, and preferably by at least about one day. In addition, a shuttle program can involve the use of the effective composition on a regular basis in the feed supply in conjunction with periodic administrations of antibiotics according to well known methods of antibiotic use.

The amount of the effective composition used in administrations in a shuttle program will typically be the same as discussed above for other uses of the effective compound. The amount of antibiotics used in a shuttle program will typically be the same as other uses of antibiotics in animal breeding and will vary between antibiotics.

In a shuttle program, the effective compound and antibiotics can be used in either a preventative or curative manner. If used in a preventative manner, the shuttle program should be initiated shortly after birth of the food animal to prevent the initial colonization of the intestinal track with pathogenic bacteria. Such preventative use should preferably start within about two days of birth. However, it should be recognized that when used in a preventative manner, a shuttle program can be initiated at any time to food animals that are not colonized by pathogenic bacteria.

A shuttle program can also be used in a curvative manner. When a food animal becomes infected with pathogenic bacteria, the use of a shuttle program can effectively slow the growth of, reduce, or eliminate the infection.

The following experimental results are provided for purposes of illustration and are not intended to limit the scope of the invention. The bacterial strains in the following examples were obtained from Colorado Animal Research Enterprises, Inc., 6200 E. County Road 56, Ft. Collins, Colo. 80524.

EXPERIMENTAL

Example 1

A strain of *Salmonella typhimurium*, species source poultry, obtained from Lilly, No. 289-1 was tested for the ability to metabolize Neosugar P. This ability was measured by acid production as measured by Phenol Red Broth Base (PRB). Growth, as measured by turbidity, was also tested.

A fermentation medium of PRB (Difco) was prepared and sterilized according to manufacturer's instructions. PRB is a defined medium which lacks a carbohydrate source. If an added carbohydrate source, such as Neosugar P, is fermented, the medium turns yellow as a positive response due to acid formed by the fermentation. 5.0 ml of the PRB was dispended into 10 test tubes. A 70% solution of Neosugar P was diluted by 1:7 in deionized water and filter sterilized. 0.5 ml of the diluted, sterile Neosugar P solution was aseptically added to individual PRB tubes to provide a 1.0% concentration of sugar in each tube. Five of the ten tubes were overlaid with mineral oil to simulate anaerobic conditions. After incubation at 37° C.±1° C., acid production and growth were measured at 24, 48, and 72 hours. The strain was also tested for viability on Tryptic-Soy (T-Soy) Agar plates and tested for presence of Salmonella on Salmonella-Shigella (SS) Agar Plates. The results of these tests are provided in Table 1.

The symbol "w+" means "weak positive", "+" means "positive", "++" means "strong positive", "+++" means "strongest positive", and "—" means "no detectable positive response".

TABLE 1

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | — | — | + | + | ++ |

TABLE 1-continued

| Test Tube | S. typhimurium | | | | | |
|---|---|---|---|---|---|---|
| | Acid Formation | | | Growth | | |
| | 24 | 48 | 72 | 24 | 48 | 72 |
| 2 | w+ | — | — | + | + | ++ |
| 3 | w+ | — | — | + | + | ++ |
| 4 | w+ | — | — | + | + | ++ |
| 5 | w+ | — | — | + | + | ++ |
| 6* | w+ | — | — | + | + | ++ |
| 7* | w+ | — | — | + | + | ++ |
| 8* | w+ | — | — | + | + | ++ |
| 9* | w+ | — | — | + | + | ++ |
| 10* | w+ | — | — | + | + | ++ |

SS Agar - very good growth: yellow; some black colonies
T-Soy Agar - very good growth
*anaerobic

Example 2

A strain of *Salmonella typhimurium* from cattle, FDA No. 2952 was tested according to the procedure in Example 1. The results of these tests are provided in Table 2.

TABLE 2

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | — | — | + | + | ++ |
| 2 | w+ | — | — | + | + | ++ |
| 3 | w+ | — | — | + | + | ++ |
| 4 | w+ | — | — | + | + | ++ |
| 5 | w+ | — | — | + | + | ++ |
| 6* | w+ | — | — | + | + | ++ |
| 7* | w+ | — | — | + | + | ++ |
| 8* | w+ | — | — | + | + | ++ |
| 9* | w+ | — | — | + | + | ++ |
| 10* | w+ | — | — | + | + | ++ |

SS Agar - very good growth; yellow; some black colonies
T-Soy Agar - very good growth
*anaerobic

Example 3

A strain of *Salmonella typhimurium*, from cattle, NVSL No. 82-4481, was tested according to the procedure in Example 1. The results of these tests are provided in Table 3.

TABLE 3

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | — | — | + | + | ++ |
| 2 | w+ | — | — | + | + | ++ |
| 3 | w+ | — | — | + | + | ++ |
| 4 | w+ | — | — | + | + | ++ |
| 5 | w+ | — | — | + | + | ++ |
| 6* | w+ | w+ | — | + | + | ++ |
| 7* | w+ | — | — | + | + | ++ |
| 8* | w+ | — | — | + | + | ++ |
| 9* | w+ | — | — | + | + | ++ |
| 10* | w+ | — | — | + | + | ++ |

SS Agar - good growth; yellow; black colonies
T-Soy Agar - very good growth
*anaerobic

Example 4

A strain of *Salmonella typhimurium* from swine, NVSL No. 83-31641-4807 was tested according to the procedure in Example 1. The results of these tests are provided in Table 4.

TABLE 4

| Test Tube | Acid Formation | | | Growth | | |
|---|---|---|---|---|---|---|
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | w+ | w+ | − | + | + | ++ |
| 7* | w+ | w+ | − | + | + | ++ |
| 8* | w+ | − | − | + | + | ++ |
| 9* | w+ | − | − | + | + | ++ |
| 10* | w+ | − | − | + | + | ++ |

*S. typhimurium*

SS Agar - good growth; yellow; black colonies
T-Soy Agar - good growth
*anaerobic

Example 5

A strain of *Salmonella typhimurium* from swine, NVSL No. 83-31296-4756 was tested according to the procedure in Example 1. The results of these tests are provided in Table 5.

TABLE 5

| Test Tube | Acid Formation | | | Growth | | |
|---|---|---|---|---|---|---|
| | 24 | 48 | 72 | 24 | 48 | 72 |
| 1 | w+ | − | − | + | + | ++ |
| 2 | − | w+ | − | + | + | ++ |
| 3 | w+ | − | − | + | + | ++ |
| 4 | w+ | − | − | + | + | ++ |
| 5 | − | − | − | + | + | ++ |
| 6* | w+ | w+ | − | + | + | ++ |
| 7* | w+ | w+ | − | + | + | ++ |
| 8* | w+ | − | − | + | + | ++ |
| 9* | w+ | − | − | + | + | ++ |
| 10* | w+ | − | − | + | + | ++ |

*S. typhimurium*

SS Agar - good growth; yellow; some black
T-Soy Agar - good growth
*anaerobic

Example 6

A strain of *Escherichia coli* from poultry, Pfizer No. BO28, was tested according to the procedure in Example 1. The results of these tests are provided in Table 6.

TABLE 6

| Test Tube | Acid Formation | | | Growth | | |
|---|---|---|---|---|---|---|
| | 24 | 48 | 72 | 24 | 48 | 72 |
| 1 | − | − | − | + | + | ++ |
| 2 | − | − | − | + | + | ++ |
| 3 | w+ | − | − | + | + | ++ |
| 4 | w+ | − | − | + | + | ++ |
| 5 | w+ | − | − | + | + | ++ |
| 6* | + | w+ | − | + | + | ++ |
| 7* | + | w+ | − | + | + | ++ |
| 8* | + | w+ | − | + | + | ++ |
| 9* | + | w+ | − | + | + | ++ |
| 10* | + | w+ | − | + | + | ++ |

*E. coli*

SS Agar - single colony; black red
T-Soy Agar - good growth; 2–3 mm
*anaerobic

Example 7

A strain of *Escherichia coli* from poultry, NVSL No. 80-430 was tested according to the procedure in Example 1. The results of these tests are provided in Table 7.

TABLE 7

| Test Tube | Acid Formation | | | Growth | | |
|---|---|---|---|---|---|---|
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | ++ | + | w+ | + | + | ++ |
| 7* | ++ | + | w+ | + | + | ++ |
| 8* | ++ | + | w+ | + | + | ++ |
| 9* | ++ | + | w+ | + | + | ++ |
| 10* | ++ | + | w+ | + | + | ++ |

*E. coli*

SS Agar - no growth
T-Soy Agar - good growth; 2 mm; motile
*anaerobic

Example 8

A strain of *Escherichia coli* from cattle, NVSL No. 85-688 was tested according to the procedure in Example 1. The results of these tests are provided in Table 8.

TABLE 8

| Test Tube | Acid Formation | | | Growth | | |
|---|---|---|---|---|---|---|
| | 24 | 48 | 72 | 24 | 48 | 72 |
| 1 | w+ | − | − | + | + | +++ |
| 2 | w+ | − | − | + | + | +++ |
| 3 | w+ | − | − | + | + | +++ |
| 4 | w+ | − | − | + | + | +++ |
| 5 | w+ | − | − | + | + | +++ |
| 6* | + | + | w+ | + | + | +++ |
| 7* | + | + | w+ | + | + | +++ |
| 8* | + | + | w+ | + | + | +++ |
| 9* | + | + | w+ | + | + | +++ |
| 10* | + | + | w+ | + | + | +++ |

*E. coli*

SS Agar - single colony; black red
T-Soy Agar - good growth; 2–3 mm
*anaerobic

Example 9

A strain of *Escherichia coli* from swine, University of Guelp, G491 was tested according to the procedure in Example 1. The results of these tests are provided in Table 9.

TABLE 9

| Test Tube | Acid Formation | | | Growth | | |
|---|---|---|---|---|---|---|
| | 24 | 48 | 72 | 24 | 48 | 72 |
| 1 | w+ | w+ | +++ | + | + | +++ |
| 2 | w+ | w+ | +++ | + | + | +++ |
| 3 | w+ | w+ | +++ | + | + | +++ |
| 4 | w+ | w+ | +++ | + | + | +++ |
| 5 | w+ | w+ | +++ | + | + | +++ |
| 6* | ++ | ++ | +++ | + | + | +++ |
| 7* | ++ | ++ | +++ | + | + | +++ |
| 8* | ++ | ++ | +++ | + | + | +++ |
| 9* | ++ | ++ | +++ | + | + | +++ |
| 10* | ++ | ++ | +++ | + | + | +++ |

*E. coli*

SS Agar - selected colonies; pink/red
T-Soy Agar - good growth; 2–3 mm
*anaerobic

Example 10

A strain of *Escherichia coli* from swine, NVSL No. 85-746 was tested according to the procedure in Example 1. The results of these tests are provided in Table 10.

TABLE 10

| Test Tube | E. coli Acid Formation 24 | 48 | 72 | Growth 24 | 48 | 72 |
|---|---|---|---|---|---|---|
| 1 | ++ | ++ | +++ | ++ | ++ | +++ |
| 2 | ++ | ++ | +++ | ++ | ++ | +++ |
| 3 | ++ | ++ | +++ | ++ | ++ | +++ |
| 4 | ++ | ++ | +++ | ++ | ++ | +++ |
| 5 | ++ | ++ | +++ | ++ | ++ | +++ |
| 6* | +++ | +++ | +++ | ++ | ++ | +++ |
| 7* | +++ | +++ | +++ | ++ | ++ | +++ |
| 8* | +++ | +++ | +++ | ++ | ++ | +++ |
| 9* | +++ | +++ | +++ | ++ | ++ | +++ |
| 10* | +++ | +++ | +++ | ++ | ++ | +++ |

SS Agar - no growth
T-Soy Agar - very good growth; 3 mm; motile
*anaerobic

Example 11

A strain of *Streptococcus faecalis* obtained from the Center for Disease Control, STR-11 was tested according to the procedure in Example 1. The results of these tests are provided in Table 11.

TABLE 11

| Test Tube | Streptococcus faecalis Acid Formation 24 | 48 | 72 | Growth 24 | 48 | 72 |
|---|---|---|---|---|---|---|
| 1 | ++ | +++ | +++ | + | ++ | +++ |
| 2 | ++ | +++ | +++ | + | ++ | +++ |
| 3 | ++ | +++ | +++ | + | ++ | +++ |
| 4 | ++ | +++ | +++ | + | ++ | +++ |
| 5 | ++ | +++ | +++ | + | ++ | +++ |
| 6* | ++ | +++ | +++ | + | ++ | +++ |
| 7* | ++ | +++ | +++ | + | ++ | +++ |
| 8* | ++ | +++ | +++ | + | ++ | +++ |
| 9* | ++ | +++ | +++ | + | ++ | +++ |
| 10* | ++ | +++ | +++ | + | ++ | +++ |

SS Agar - no growth
T-Soy Agar - small white colonies
*anaerobic

Example 12

A strain of *Streptococcus faecalis* obtained from Colorado State University Microbiology Department Culture Collection was tested according to the procedure in Example 1. The results of these tests are provided in Table 12.

TABLE 12

| Test Tube | Streptococcus faecalis Acid Formation 24 | 48 | 72 | Growth 24 | 48 | 72 |
|---|---|---|---|---|---|---|
| 1 | ++ | +++ | +++ | + | ++ | +++ |
| 2 | ++ | +++ | +++ | + | ++ | +++ |
| 3 | ++ | +++ | +++ | + | ++ | +++ |
| 4 | ++ | +++ | +++ | + | ++ | +++ |
| 5 | ++ | +++ | +++ | + | ++ | +++ |
| 6* | ++ | +++ | +++ | + | ++ | +++ |
| 7* | ++ | +++ | +++ | + | ++ | +++ |
| 8* | ++ | +++ | +++ | + | ++ | +++ |
| 9* | ++ | +++ | +++ | + | ++ | +++ |
| 10* | ++ | +++ | +++ | + | ++ | +++ |

SS Agar - no growth
T-Soy Agar - small white colonies; 1 mm
*anaerobic

Example 13

A strain of *Lactobacillus plantarum*, obtained from Colorado State University Microbiology Department Culture Collection was tested according to the procedure in Example 1. The results of these tests are provided in Table 13.

TABLE 13

| Test Tube | Lactobacillus plantarum Acid Formation 24 | 48 | 72 | Growth 24 | 48 | 72 |
|---|---|---|---|---|---|---|
| 1 | + | ++ | +++ | w+ | + | ++ |
| 2 | + | ++ | +++ | w+ | + | ++ |
| 3 | + | ++ | +++ | w+ | + | ++ |
| 4 | + | ++ | +++ | w+ | + | ++ |
| 5 | − | ++ | +++ | − | + | ++ |
| 6* | + | ++ | +++ | w+ | + | ++ |
| 7* | + | ++ | +++ | w+ | + | ++ |
| 8* | + | ++ | +++ | w+ | + | ++ |
| 9* | + | ++ | +++ | w+ | + | ++ |
| 10* | + | ++ | +++ | w+ | + | ++ |

SS Agar - no growth
T-Soy Agar - poor growth; very small colonies
*anaerobic

From the above experiments in Examples 1–13, it can be seen that the Salmonella strains exhibited little fermentation activity as measured by acid formation. While all strains showed some initial "weak positive" results, this initial activity likely indicates fermentation of the glucose in the Neosugar composition.

All of the Salmonella strains showed consistent moderate growth as measured by turbidity. The lack of fermentation while growth occurred indicates that the Neosugar was not the energy or carbon source for any growth of Salmonella. It appears, therefore, that some other energy and carbon source, such as, for example, amino acids, in the PRB was used by Salmonella. The fact that Salmonella is able to grow in the presence of Neosugar indicates that, although the organism is unable to ferment the fructo-oligosaccharides in Neosugar, these compositions are not toxic to Salmonella at the concentrations in these tests.

Example 14

One hundred ninety-two chicks were obtained from a local hatchery on the day of hatching and transported to the Russell Research Center of the United States Department of Agriculture, Agricultural Research Service in Athens, Georgia. All of the chicks were fed non-medicated broiler starter crumble feed ad libitum for the duration of the experiment. Chicks were housed in isolation units at the Poultry Disease Research Center at the University of Georgia. Chicks were randomly placed in groups of six or twelve in isolation units. The groups were challenged with Salmonella at either day 2 or day 14 with does of Salmonella of either $10^3$, $10^6$ or $10^9$. Chicks were then either not stressed, stressed at day 20, stressed at day 13, or stressed at days 13 and 20. The groups then received either no Neosugar treatment or 0.75% by weight Neosugar-G in syrup form mixed into the feed. On day 21, the chicks were killed by cervical dislocation and analyzed for the presence of Salmonella by the procedures of Bailey, et al., *Effect of Anticoccidial and Antimicrobial Feed Additives on Prevention of Salmonella Colonization of Chicks Treated with Anaerobic Cultures of Chicken Feces*, Avian Disease, v. 32, pp. 324–29 (1988). The results of these experiments are shown below in Table 14.

TABLE 14

| Pen | Challenge: Day | Dose | Stress Day | 0.75% Neosugar | # infected # treated | CF* |
|---|---|---|---|---|---|---|
| 1 | 2 | $10^6$ | 20 | NO | 2/12 | 0.25 |

TABLE 14-continued

| Pen | Challenge: Day | Dose | Stress Day | 0.75% Neosugar | # infected / # treated | CF* |
|---|---|---|---|---|---|---|
| | | | | NO | 2/12 | 0.25 |
| 2 | 14 | $10^3$ | — | NO | 0/6 | — |
| | | | 20 | NO | 0/6 | — |
| | | | 13 | NO | 0/6 | — |
| | | | 13,20 | NO | 0/6 | — |
| 3 | 14 | $10^6$ | — | NO | 1/6 | 0.6 |
| | | | 20 | NO | 1/6 | 0.3 |
| | | | 13 | NO | 1/6 | 0.3 |
| | | | 13,20 | NO | 1/6 | 0.3 |
| 4 | 14 | $10^9$ | — | NO | 1/6 | 0.3 |
| | | | 20 | NO | 2/6 | 0.7 |
| | | | 13 | NO | 6/6 | 2.8 |
| | | | 13,20 | NO | 6/6 | 2.4 |
| 5 | 2 | $10^6$ | 20 | YES | 1/12 | 0.1 |
| | | | — | YES | 3/12 | 0.4 |
| 6 | 14 | $10^3$ | — | YES | 0/6 | — |
| | | | 20 | YES | 0/6 | — |
| | | | 13 | YES | 0/6 | — |
| | | | 13,20 | YES | 0/6 | — |
| 7 | 14 | $10^6$ | — | YES | 0/6 | — |
| | | | 20 | YES | 1/6 | 0.3 |
| | | | 13 | YES | 1/6 | 0.3 |
| | | | 13,20 | YES | 1/6 | 0.3 |
| 8 | 14 | $10^9$ | — | YES | 2/6 | 0.5 |
| | | | 20 | YES | 2/6 | 0.5 |
| | | | 13 | YES | 3/6 | 0.8 |
| | | | 13,20 | YES | 3/6 | 0.8 |

*CF - Colonization Factor = Mean number of Salmonella per gram of ceca and contents for all birds within a treatment group.

The results of the experiments in Example 14 demonstrate the effectiveness of the use of Neosugar in the reduction in the colonization of chickens by Salmonella. In particular, as shown by the results in pens 4 and 8, when chicks are stressed prior to Salmonella challenge, the inclusion of Neosugar in the diet is particularly effective. Specifically, the rate of infection (#infected/#treated) was reduced from 6/6 and 6/6 to 3/6 and 3/6. Moreover, the degree of infection, i.e., CF, was reduced from 2.8 and 2.4 to 0.8 and 0.8.

Example 15

Seventy-eight chicks were obtained from a local hatchery on the day of hatching and transported to the Russell Research Center of the United States Department of Agriculture, Agricultural Research Service, in Athens, Ga. All chicks were fed non-medicated broiler starter crumble feed ad libitum for the duration of the experiment. Chicks were housed in isolation units at the Poultry Disease Research Center at the University of Georgia. Chicks were randomly placed six to an isolation unit. One group of chicks received 0.2 ml of a 48-hour old anaerobically incubated competitive exclusion (CE) broth culture of fecal material from pathogen free adult chickens before being placed in the isolation unit. Chicks were given plain water or water with two percent (2%) Neosugar—P in syrup form or two percent (2%) arabinose for the duration of the experiment. At either day 2 or day 7, the chicks were challenged with a dose of Salmonella. On day 14, the chicks were killed by cervical dislocation and analyzed for the presence of Salmonella by the procedures of Bailey, et al., *Effect of Anticoccidial and Antimicrobial Feed Additives on Prevention of Salmonella Colonization of Chickens Treated With Anaerobic Cultures of Chicken Feces*, Avian Disease, v. 32, pp. 324–329 (1988).

TABLE 15

| Treatment | Challenge Day | Challenge Level | # infected / # treated | CF* |
|---|---|---|---|---|
| None | 2 | $10^6$ | 6/6 | 1.9 |
| CE (day 0) | 2 | $10^6$ | 0/6 | — |
| 2% NS (day 3-14) | 2 | $10^6$ | 2/6 | 0.7 |
| 2% Ara (day 3-14) | 2 | $10^6$ | 6/6 | 1.9 |
| None | 7 | $10^4$ | 0/6 | — |
| None | 7 | $10^6$ | 0/6 | — |
| None | 7 | $10^8$ | 2/6 | 0.5 |
| 2% NS (day 0-14) | 7 | $10^4$ | 0/6 | — |
| 2% NS (day 0-14) | 7 | $10^6$ | 0/6 | — |
| 2% NS (day 0-14) | 7 | $10^8$ | 0/6 | — |
| 2% Ara (day 0-14) | 7 | $10^4$ | 1/6 | 0.25 |
| 2% Ara (day 0-14) | 7 | $10^6$ | 0/6 | — |
| 2% Ara (day 0-14) | 7 | $10^8$ | 1/6 | 0.25 |

*CF = Colonization Factor = Mean number of Salmonella per gram 20 of ceca and contents for all birds within a treatment group.

Of the four treatments with a Salmonella challenge on the second day, both the CE treatment and the Neosugar treatment showed a reduction in the number of infected chicks with respect to the number of treated chicks and of the two chicks in the Neosugar treatment which were infected, they had a low colonization factor. Of the treatments receiving a Salmonella challenge at day 7, while the Neosugar and arabinose treatments produced almost no infected birds, the controls were substantially not infected, as well. Therefore, the low rate of infection for the Neosugar and arabinose treatments for the Salmonella challenge at day 7 are inconclusive.

Example 16

An experimental protocol as described in Example 14 was conducted on another set of 72 chicks. The treatments consisted either of no treatment, 2% by weight Neosugar—P in syrup form in water, or CE culture. The chicks were killed at either day 8 or day 13. The results of these procedures are provided below in Table 16.

TABLE 16

| Treatment | Challenge | Kill Day | # infected / # treated | CF |
|---|---|---|---|---|
| None | $10^4$-day 2 | 8 | 4/6 | 1.4 |
| None | $10^6$-day 2 | 8 | 5/6 | 2.8 |
| 2% NS (day 0-8) | $10^4$-day 2 | 8 | 3/6 | 1.9 |
| 2% NS (Day 0-8) | $10^6$-day 2 | 8 | 5/6 | 2.0 |
| 2% NS (day 3-8) | $10^6$-day 2 | 8 | 6/6 | 3.6 |
| CE - day 0 | $10^6$-day 2 | 8 | 2/6 | 0.5 |
| None | $10^6$-day 7 | 13 | 2/6 | 0.5 |
| None | $10^9$-day 7 | 13 | 3/7 | 3.0 |
| 2% NS (day 0-13) | $10^6$-day 7 | 13 | 0/6 | — |
| 2% NS (day 0-13) | $10^9$-day 7 | 13 | 3/4 | 2.2 |
| 2% NS (day 3-13) | $10^6$-day 2 | 13 | 5/7 | 2.1 |
| None | None | 13 | 0/6 | — |

The results of the procedures in Example 16 appear to be inconclusive because the controls had highly variable rates of infection (# infected/# treated) and degrees of infection (CF).

Example 17

Chicks were obtained from a local hatchery near the Russell Research Center on the day of hatching and transported to the Russell Research Center of the United States Department of Agriculture, Agricultural Research Service, in Athens, Ga. All chicks were fed non-medicated broiler starter crumble feed ad libitum. Chicks were housed in isolation units at the Poultry Disease Research Center at the University of Georgia.

Chicks in groups of four through seven were randomly placed in isolation units. The chicks were given one of four treatments. The first was no treatment at all; the second was 0.375% by weight Neosugar—P in syrup form deposited on a microcrystalline cellulose carrier in the feed ration; the third was a 0.2 ml of a 48-hour old undefined CE culture on day 0; and the fourth was a combination of the CE administration and Neosugar in the food ration. A Salmonella challenge was made at either day one or day seven by gavaging 0.2 ml of a 24-hour culture of *S. typhimurium*. The results are shown below in Table 17.

TABLE 17

| Pen # | Treatment | Challenge Day | Challenge Level | Kill Day | # infected / # treated | CF |
|---|---|---|---|---|---|---|
| 1 | none | 1 | $10^4$ | 8 | 5/5 | 3.7 |
| 2 | none | 1 | $10^6$ | 8 | 6/6 | 3.5 |
| 3 | none | 1 | $10^8$ | 8 | 4/4 | 5.7 |
| 4 | none | 7 | $10^6$ | 14 | 7/7 | 2.7 |
| 5 | none | 7 | $10^8$ | 14 | 6/6 | 2.6 |
| 6 | none | 7 | $10^9$ | 14 | 5/6 | 1.7 |
| 7 | NS | 1 | $10^4$ | 8 | 5/5 | 4.3 |
| 8 | NS | 1 | $10^6$ | 8 | 6/6 | 4.9 |
| 9 | NS | 1 | $10^8$ | 8 | 5/5 | 4.5 |
| 10 | NS | 7 | $10^6$ | 14 | 5/6 | 2.0 |
| 11 | NS | 7 | $10^8$ | 14 | 6/6 | 2.8 |
| 12 | NS | 7 | $10^9$ | 14 | 4/5 | 2.1 |
| 13 | CE | 1 | $10^4$ | 8 | 4/6 | 1.2 |
| 14 | CE | 1 | $10^6$ | 8 | 5/6 | 1.7 |
| 15 | CE | 1 | $10^8$ | 8 | 5/6 | 1.8 |
| 16 | CE | 7 | $10^6$ | 14 | 0/4 | — |
| 17 | CE | 7 | $10^8$ | 14 | 0/4 | — |
| 18 | CE | 7 | $10^9$ | 14 | 2/4 | 1.3 |
| 19 | CE + NS | 1 | $10^4$ | 8 | 5/5 | 1.5 |
| 20 | CE + NS | 1 | $10^6$ | 8 | 6/6 | 3.3 |
| 21 | CE + NS | 1 | $10^8$ | 8 | 6/6 | 3.7 |
| 22 | CE + NS | 7 | $10^6$ | 14 | 4/4 | 2.0 |
| 23 | CE + NS | 7 | $10^8$ | 14 | 1/4 | 0.4 |
| 24 | CE + NS | 7 | $10^9$ | 14 | 1/4 | 0.4 |

The results from this set of experiments indicate that the combination of using CE cultures and Neosugar can reduce the number of infected chicks as well as the degree of infection. In particular, pen numbers 22–24, which received the CE and Neosugar treatment with a Salmonella challenge at day 7 had low rates of infection and/or low colonization factors.

Example 18

Broiler chicks from a hatchery near the Russell Research Center of the United States Department of Agriculture, Agricultural Research Service, Athens, Ga., were started on the day of hatching on non-medicated broiler starter crumble feed ad libitum. Some of the groups of chicks had 0.75% by weight Neosugar—P in syrup form deposited on a mircocrystalline cellulose carrier mixed with the feed. Some of the groups of chicks also received CE cultures. The chicks were challenged with Salmonella at either day 7 or day 14. The chicks were killed and examined for the presence of Salmonella seven days after the challenge. The results of this experiment are found below in Table 18.

TABLE 18

| Pen # | Treatment | Challenge Day | Challenge Level | # infected / # treated | CF |
|---|---|---|---|---|---|
| 1 | none | 7 | $10^6$ | 6/6 | 7.7 |
| 2 | none | 7 | $10^9$ | 7/7 | 6.3 |
| 3 | none | 14 | $10^6$ | 8/8 | 3.6 |
| 4 | none | 14 | $10^9$ | 8/8 | 6.1 |
| 5 | NS | 7 | $10^6$ | 7/7 | 6.6 |
| 6 | NS | 7 | $10^9$ | 8/8 | 5.7 |
| 7 | NS | 14 | $10^6$ | 8/8 | 5.5 |
| 8 | NS | 14 | $10^9$ | 8/8 | 5.3 |
| 9 | CE | 7 | $10^6$ | 8/8 | 1.7 |
| 10 | CE | 7 | $10^9$ | 8/8 | 2.0 |
| 11 | CE | 14 | $10^6$ | 7/7 | 3.2 |
| 12 | CE | 14 | $10^9$ | 8/8 | 5.1 |
| 13 | CE + NS | 7 | $10^6$ | 0/4 | — |
| 14 | CE + NS | 7 | $10^9$ | 2/6 | 0.7 |
| 15 | CE + NS | 14 | $10^6$ | 6/8 | 1.7 |
| 16 | CE + NS | 14 | $10^9$ | 5/5 | 6.1 |

The results in the experiments in Example 18 indicate that the combination of using a CE culture and Neosugar in combination has a synergistic effect. The chicks in pens 13 and 14 had low rates of infection and low colonization factors. The chicks in pen 15 having the combined treatment with the lower level challenge at day 14 had a somewhat lower rate of infection and a low colonization factor.

Example 19

Broiler chicks from a hatchery near the Russell Research Center of the United States Department of Agriculture, Agriculture Research Service, Athens, Ga., were started on the day of hatching on non-medicated broiler starter crumble feed ad libitum. Some of the groups of chicks had 0.75% by weight Neosugar—P in syrup from deposited on a microcrystalline cellulose carrier mixed with the feed. Some of the groups of chicks also received CE cultures. The chicks were challenged with Salmonella at either day 7 or day 14. The chicks were killed and examined for the presence of Salmonella seven days after the challenge. The results of this experiment are found below in Table 19.

TABLE 19

| Pen # | Treatment | Challenge Day | Challenge Level | # infected / # treated | CF |
|---|---|---|---|---|---|
| 1 | none | 7 | $10^6$ | 4/15 | 0.4 |
| 2 | none | 7 | $10^9$ | 14/15 | 3.0 |
| 3 | none | 14 | $10^6$ | 0/15 | — |
| 4 | none | 14 | $10^9$ | 5/15 | 0.6 |
| 5 | NS | 7 | $10^6$ | 1/15 | 0.1 |
| 6 | NS | 7 | $10^9$ | 12/15 | 2.1 |
| 7 | NS | 14 | $10^6$ | 1/15 | 0.2 |
| 8 | NS | 14 | $10^9$ | 4/15 | 0.7 |
| 9 | CE | 7 | $10^6$ | 2/15 | 0.2 |
| 10 | CE | 7 | $10^9$ | 6/15 | 0.9 |
| 11 | CE | 14 | $10^6$ | 1/15 | 0.1 |
| 12 | CE | 14 | $10^9$ | 1/15 | 0.1 |
| 13 | CE + NS | 7 | $10^6$ | 2/15 | 0.2 |
| 14 | CE + NS | 7 | $10^9$ | 2/15 | 0.4 |
| 15 | CE + NS | 14 | $10^6$ | 3/15 | 0.3 |
| 16 | CE + NS | 14 | $10^9$ | 3/15 | 0.4 |

The results from the experiments in Example 19 are inconclusive because the control treatments failed to produce significant Salmonella infection. Therefore, even though the rate of infection and colonization factors for all other treatments were relatively low, no conclusions can be drawn from these procedures.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A method for inhibiting the growth of Salmonella in the presence of microflora other than Salmonella in the intestinal tract of a food animal, comprising:
   (a) introducing a composition that is fermented by said other microflora at a rate competitively greater than the rate at which said composition is fermented by Salmonella to said intestinal tract of said food animal; and
   (b) introducing a competitive exclusion culture to said intestinal tract of said food animal.

2. The method as claimed in claim 1, wherein said food animal is a chicken.

3. The method as claimed in claim 2, wherein said chicken is less than two days old.

4. The method as claimed in claim 2, wherein said competitive exclusion culture is an undefined culture of intestinal microflora from a non-infected chicken.

5. The method as claimed in claim 4, wherein said non-infected chicken is at least three weeks old.

6. The method as claimed in claim 1, wherein said competitive exclusion culture is a defined culture of intestinal microflora.

7. The method as claimed in claim 1, wherein said composition comprises a fructooligosaccharide.

8. A method as claimed in claim 7, wherein said composition comprises between about 0.05% by weight and about 5% by weight fructooligosaccharide.

9. The method as claimed in claim 1, wherein said composition includes compounds selected from the group consisting of 1-kestose, nystose, 1-fructofuranosylnystose and mixtures thereof.

10. The method as claimed in claim 9, wherein said composition comprises between about 20% by weight and about 40% by weight 1-kestose, between about 20% by weight and about 50% by weight nystose, and between about 5% by weight and about 15% by weight 1-fructofuranosylnystose.

11. The method as claimed in claim 1, wherein said composition comprises sucrose molecules having from 1 to 8 fructose residues attached to the sucrose molecules.

12. The method as claimed in claim 1, wherein said composition is a saccharide.

13. The method as claimed in claim 12, wherein said composition is selected from the group consisting of monosaccharides, disaccharides and oligosaccharides.

14. The method as claimed in claim 1, wherein said composition is lactose.

15. A method for inhibiting the growth of Salmonella in the presence of microflora other than Salmonella in the intestinal tract of a food animal, comprising:
   (a) introducing a composition that is fermented by said other microflora to produce metabolites that inhibit the growth of Salmonella to said intestinal tract of said food animal; and
   (b) introducing a competitive exclusion culture to said intestinal tract of said food animal.

16. The method as claimed in claim 15, wherein said food animal is a chicken.

17. The method as claimed in claim 16, wherein said chicken is less than two days old.

18. The method as claimed in claim 16, wherein said competitive exclusion culture is an undefined culture of intestinal microflora from a non-infected chicken.

19. The method as claimed in claim 18, wherein said non-infected chicken is at least three weeks old.

20. The method as claimed in claim 15, wherein said competitive exclusive culture is a defined culture of intestinal microflora.

21. A mixture for inhibiting the growth of Salmonella in a mixed microfloral population including microflora other than Salmonella, comprising:
   a composition which is fermented by said other microflora at a rate competitively greater than the rate at which said composition is fermented by Salmonella; and
   a competitive exclusion culture.

22. The mixture claimed in claim 21, wherein said composition is a saccharide.

23. The mixture claimed in claim 22, wherein said composition is selected from the group consisting of monosaccharides, disaccharides and oligosaccharides.

24. The mixture claimed in claim 21, wherein said composition is lactose.

25. The mixture claimed in claim 21, wherein said competitive exclusion culture is an undefined culture of intestinal microflora from a non-infected chicken.

26. The mixture claimed in claim 21, wherein said competitive exclusion culture is a defined culture of intestinal microflora.

27. The mixture claimed in claim 21, wherein said composition comprises a fructooligosaccharide.

28. The mixture claimed in claim 21, wherein said composition includes compounds selected from the group consisting of 1-kestose, nystose, 1-fructofuranosylnystose and mixtures thereof.

29. The mixture claimed in claim 28, wherein said composition comprises between about 20% by weight and about 40% by weight 1-kestose, between about 20% by weight and about 50% by weight nystose, and between about 5% by weight and about 15% by weight 1-fructofuranosylnystose.

30. The mixture claimed in claim 21, wherein said composition comprises sucrose molecules having from 1 to 8 fructose residues attached to the sucrose molecules.

31. The mixture claimed in claim 21, wherein said microflora other than Salmonella comprise a population of microflora selected from the group consisting of Lactobacillus, Streptococcus, and mixed populations thereof.

32. A mixture for inhibiting the growth of Salmonella in a mixed microfloral population including microflora other than Salmonella, comprising:
   a composition, wherein said microflora other than Salmonella produce metabolites that inhibit the growth of Salmonella upon fermentation of said composition; and
   a competitive exclusion culture.

33. The mixture claimed in claim 32, wherein said competitive exclusion culture is an undefined culture of intestinal microflora from a non-infected chicken.

34. The mixture claimed in claim 32, wherein said competitive exclusion culture is a defined culture of intestinal microflora.

* * * * *

UNITED STATES PATENT AND TRADEMARK OFFICE
CERTIFICATE OF CORRECTION

PATENT NO. : 5,032,579

DATED : July 16, 1991

INVENTOR(S) : Speights, et al.

It is certified that error appears in the above-identified patent and that said Letters Patent is hereby corrected as shown below:

On Title page

In the Abstract, line 11, delete "fructo-oligosaccharidesa" and insert -- fructo-oligosaccharides-- therefor.

In the Abstract, line 17, delete "anomal" and insert -- animal -- therefor.

Column 9, line 50, delete "lift" and insert -- life -- therefor.

Column 18, Table 15, line 16, delete "20".

Column 20, line 31, delete "from" and insert -- form -- therefor.

Signed and Sealed this

Twenty-ninth Day of December, 1992

Attest:

DOUGLAS B. COMER

Attesting Officer

Acting Commissioner of Patents and Trademarks